United States Patent [19]
Wong et al.

[11] Patent Number: 5,811,557
[45] Date of Patent: Sep. 22, 1998

[54] PREPARATION OF MIBEFRADIL VIA AN ACETONITRILE ANION

[75] Inventors: Jim-wah Wong, Boulder; Peter J. Harrington, Louisville, both of Colo.

[73] Assignee: Roche Colorado Corporation, Boulder, Colo.

[21] Appl. No.: 60,401

[22] Filed: Apr. 14, 1998

[51] Int. Cl.$^6$ ......................... C07D 235/14; C07C 255/33
[52] U.S. Cl. ......................... 548/309.7; 558/426
[58] Field of Search ........................... 558/426; 548/309.7

[56] References Cited

U.S. PATENT DOCUMENTS

| | | | |
|---|---|---|---|
| 4,680,310 | 7/1987 | Hengartner et al. | 514/539 |
| 4,808,605 | 2/1989 | Branca et al. | 514/394 |
| 5,120,759 | 6/1992 | Hengartner et al. | 514/452 |

OTHER PUBLICATIONS

B.M. Trost et al., "New Synthetic Reactions. Alkylation of Lactam Derivatives", *J. Org. Chem.*, 39(16), 2475–6 (1974).

R.P. Woodbury et al., "Isolation and Reactions of α–Lithio N,N–Dimethylacetamide", *J. Org. Chem.*, 42(10), 1688–90 (1977).

V. Bažant et al., "Properties of Sodium–bis–(2–methoxyethoxy)aluminiumhydride. I. Reduction of Some Organic Functional Groups", *Tetrahedron Letters*, 1968, 3303–6.

H.R. Wiltshire et al., "Metabolism of calcium antagonist Ro 40–5967 . . . ", *Xenobiotica*, 22 (7), 837–57 (1992).

S. Chandrasekaran et al., "Synthesis of Substituted β–Lactams by Addition of Nitromethane . . .", *J. Org. Chem.*, 42(24), 3972–4 (1977).

D.B. Bryan et al., "Nuclear Analogues of β–Lactam Antibiotics. 2 . . . ", *J. Am. Chem. Soc.*, 99(7), 2353–5 (1977).

G.J. O'Malley et al., "Tremorgenic Mycotoxins: Synthesis of 6–Demethyloxyfumitremorgin C", *Tetrahedron Letters*, 28(11), 1131–4 (1987).

M. Leplawy et al., "Peptides—XI. Synthesis of Peptides Derived from Alpha–Methylamine", *Tetrahedron*, 11, 39–51 (1960).

*Primary Examiner*—Laura L. Stockton
*Attorney, Agent, or Firm*—Heller Ehrman White & McAuliffe

[57] ABSTRACT

A method of preparing 2-[2-{[3-(1H-benzimidazol-2-yl)propyl]methylamino}ethyl]-6-fluoro-1-isopropyl-1,2,3,4-tetrahydronaphthalen-2-yl methoxyacetate comprises contacting 6-fluoro-1-isopropyl-3,4-dihydro-1H-naphthalen-2-one with the anion of acetonitrile in an aprotic polar solvent; contacting [3-(1H-benzitidazol-2-yl)propyl]methylamine with the thus-formed (6-fluoro-2-hydroxy-1-isopropyl-1,2,3,4-tetrahydronaphthalen-2-yl)acetonitrile in the presence of hydrogen and a hydrogenation catalyst, followed by contacting the thus-formed 2-[2-{[3-(1H-benzimidazol-2-yl)propyl]methylamino}ethyl]-6-fluoro-1-isopropyl-1,2,3,4-tetrahydronaphthalen-2-ol with methoxyacetic acid or an activated derivative of methoxyacetic acid. The invention is particularly applicable to the preparation of mibefradil, (1S,2S)-2-[2-{[3-(1H-benzimidazol-2-yl)propyl]methylamino}ethyl]-6-fluoro-1-isopropyl-1,2,3,4-tetrahydronaphthalen-2-yl methoxyacetate, and its dihydrochloride salt. (6-Fluoro-2-hydroxy-1-isopropyl-1,2,3,4-tetrahydronaphthalen-2-yl) acetonitrile is new.

20 Claims, No Drawings

PREPARATION OF MIBEFRADIL VIA AN ACETONITRILE ANION

CROSS-REFERENCE TO RELATED APPLICATIONS

This application claims the benefit under 35 USC 119(e) of Provisional Application No. 60/045,150, filed Apr. 30, 1997, which is incorporated herein by reference in its entirety.

The subject matter of this application is related to the subject matter of Application No. 09/060,151 (Attorney Docket No. 22138-1004), entitled "PREPARATION OF MIBEFRADIL VIA AN ACETAMIDE ANION", and of Application No 09/060,168 (Attorney Docket No. 22138-1005), entitled "PREPARATION OF MIBEFRADIL VIA A NAPHTHALENYLACETIC ACID", both filed simultaneously with this application. Application No. 09/060,151 claims the benefit under 35 USC 119(e) of Provisional Application No. 60/045,151, filed Apr. 30, 1997, and Application No. 09/060,168 claims the benefit under 35 USC 119(e) of Provisional Application No. 60/046,795, filed Apr. 30, 1997. These applications and other documents referred to elsewhere in the specification of this application are incorporated herein by reference in their entirety.

BACKGROUND OF THE INVENTION

This invention relates to the preparation of mibefradil and its dihydrochloride salt.

U.S. Pat. No. 4,808,605 (to Hoffinann-La Roche) discloses various calcium antagonists including mibefradil, (1S,2S)-2-[2-{[3-(1H-benzimidazol-2-yl)propyl]-methylamino }ethyl]-6-fluoro- 1-isopropyl- 1,2,3,4-tetrahydronaphthalen-2-yl methoxyacetate, the dihydrochloride salt of which is the active ingredient of the antihypertensive POSICOR®. The synthesis of mibefradil, as described in that patent, involves the reaction of (1S,2S)-6-fluoro-1-isopropyl-2-[2-(4-toluenesulfonyloxy) ethyl]-1,2,3,4-tetrahydronaphthalene-2-ol with [3-(1H-benzimidazol-2-yl)propyl]methylamine in the presence of Hunig base (ethyldiisopropylamine) to form ( 1S,2S)-2-[2-{[3-( 1H-benzimidazol-2-yl)propyl]methylamino}ethyl]-6-fluoro-1-isopropyl-1,2,3,4-tetrahydronaphthalen-2-ol, which is then acylated with methoxyacetyl chloride in chloroform in the presence of ethyldiisopropylamine to form mibefradil.

The (1S,2S)-6-fluoro-1-isopropyl-2-[2-(4-toluenesulfonyloxy)ethyl]-1,2,3,4-tetrahydronaphthalene-2-ol, as described in U.S. Pat. No. 4,680,310 (also to Hoffinann-La Roche), is prepared by reacting (s)-6-fluoro-1-isopropyl-3,4-dihydro-IH-naphthalen-2-one with tert-butyl bromoacetate in the presence of activated magnesium to form tert-butyl (1S,2S)-(6-fluoro-2-hydroxy-1-isopropyl-1,2,3,4-tetrahydro-naphthalen-2-yl) acetate, which is reduced with lithium aluminum hydride to form (1S,2S)-6-fluoro-2-(2-hydroxyethyl)-1-isopropyl-1,2,3,4-tetrahydronaphthalen-2-ol, and then reacted with 4-toluenesulfonyl chloride in pyridine to form the (1S,2S)-6-fluoro-1-isopropyl-2-[2-(4-toluenesulfonyloxy) ethyl]-1,2,3,4-tetrahydronaphthalene-2-ol.

U.S. Pat. No. 5,120,759 (also to Hoffmann-La Roche) discloses certain (1R,2R)-tetrahydronaphthalene derivatives that are enantiomers of the those compounds disclosed in U.S. Pat. No. 4,680,310, and their preparation from (R)-6-fluoro-1-isopropyl-3,4-dihydro-IH-naphthalen-2-one.

It would be of value to have a method for the preparation of mibefradil and mibefradil dihydrochloride that affords the desired compound easily and in reproducible high yield and purity, and is readily adaptable to large scale commercial production.

BRIEF SUMMARY OF THE INVENTION

In a first aspect, this invention provides the compound (6-fluoro-2-hydroxy-1-isopropyl- 1,2,3,4-tetrahydronaphthalen-2-yl) acetonitrile, and in particular its (1S,2S)-enantiomer, useful in the preparation of mibefradil and other tetrahydronaphthalene derivatives.

In a second aspect, this invention provides a method of preparing (6-fluoro-2-hydroxy-1-isopropyl- 1,2,3,4-tetrahydronaphthalen-2-yl) acetonitrile, and in particular its (1S,2S)-enantiomer, comprising contacting 6-fluoro-1-isopropyl-3,4-dihydro-1H-naphthalen-2-one, and in particular its (S)-enantiomer, with the anion of acetonitrile in an aprotic polar solvent.

In a third aspect, this invention provides a method of preparing 2-[2-{[3-(1H-benzimidazol-2-yl)propyil] methylamino}ethyl]-6-fluoro-1-isopropyl-1,2,3,4-tetrahydronaphthalen-2-ol, and in particular its (1S,2S)-enantiomer, comprising contacting [3-(1H-benzimidazol-2-yl)propyl]methylamine with (6-fluoro-2-hydroxy-1-isopropyl-1,2,3,4-tetrahydronaphthalen-2-yl) acetonitrile, and in particular its (1S,2S)-enantiomer, in the presence of hydrogen and a hydrogenation catalyst.

In a fourth aspect, this invention provides a method of preparing 2-[2-{[3-(1H-benzimidazol-2-yl)propyl] methylamino}ethyl]-6-fluoro-1-isopropyl-1,2,3,4-tetrahydronaphthalen-2-yl methoxyacetate and its acid addition salts, and in particular its (1S,2S)-enantiomer, comprising preparing 2-[2-{[3-(1H-benzimidazol-2-yl)-propyljmethylamino}ethyl]-6-fluoro-1-isopropyl-1,2,3,4-tetrahydronaphthalen-2-ol, and in particular its (1S,2S)-enantiomer, as described above, and contacting the product with methoxyacetic acid or an activated derivative of methoxyacetic acid, optionally followed by formation of an acid addition salt, especially the dihydrochloride salt.

In particular, this invention relates to the preparation of mibefradil, (1S,2S)-2-[2-{[3-(1H-benzimidazol-2-yl) propyl]methylamino )ethyl]-6-fluoro-1-isopropyl-1,2,3,4-tetrahydronaphthalen-2-yl methoxyacetate, and its dihydrochloride salt.

DETAILED DESCRIPTION OF THE INVENTION

While the invention will be generally described with reference to (1S,2S)-(6-fluoro-2-hydroxy-1-isopropyl-1,2,3,4-tetrahydronaphthalen-2-yl) acetonitrile, its preparation, and its use in the preparation of mibefradil, it will be apparent to one of ordinary skill in the art that the reaction of (R)-6-fluoro-1-isopropyl-3,4-dihydro-1H-naphthalen-2-one with acetonitrile anion will result in the preparation of (1R,2R)-(6-fluoro-2-hydroxy-1-isopropyl-1,2,3,4-tetrahydronaphthalen-2-yl) acetonitrile, which may be used to prepare the (1R,2R)-tetrahydronaphthalene derivatives of U.S. Pat. No. 5,120,759 in the same manner as the (1S,2S)-isomer is used here to prepare mibefradil. Accordingly, unless the context requires otherwise, reference to any compound is to be considered as a reference to individual enantiomers of the compound, and to racemic or non-racemic mixtures thereof The process of this invention may be represented schematically as follows:

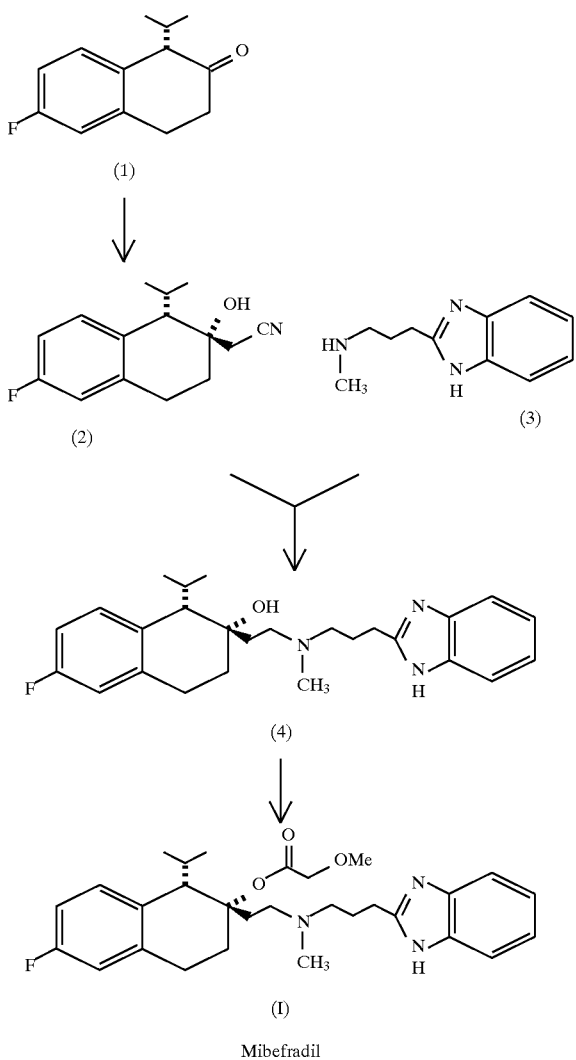

Mibefradil

Definitions

An "activated derivative" of methoxyacetic acid is a derivative that renders the acid more active in the esterification of 2-[2-{[3-(1H-benzimidazol-2-yl)propyl]methylamino}-ethyl]-6-fluoro-1-isopropyl-1,2,3,4-tetrahydronaphthalen-2-ol. Typical such derivatives include methoxyacetyl halides and methoxyacetyl anhydride, and a preferred activated derivative is methoxyacetyl chloride.

An "aprotic polar solvent" includes organic solvents that may be either water-immiscible, such as halogenated hydrocarbons, e.g. methylene chloride, or water-miscible, such as ethers, e.g. tetrahydrofuran and bis(2-methoxyethyl ether), dimethylformamide, N-methylpyrrolidone, dimethylsulfoxide, etc. The solvent may also contain minor proportions of aprotic non-polar solvents such as hydrocarbons, e.g. cyclohexane, toluene, etc., provided that the solvent properties are largely determined by the polar solvent.

Starting Materials

Compounds 1. 6-Fluoro-1-isopropyl-3,4-dihydro-1H-naphthalen-2-one and its (S)-isomer are known, for example, from U.S. Pat. No. 4,680,310, where their preparation from 2-(4-fluorophenyl)-3-methylbutyric acid and its (S)-isomer are disclosed. (R)-6-Fluoro-1-isopropyl-3,4-dihydro-1H-naphthalen-2-one is known, for example, from U.S. Pat. No. 5,120,759, where its preparation from (R)-2-(4-fluorophenyl)-3-methyl-butyric acid is disclosed.

Compound 3.[3-(1H-Benzimidazol-2-yl)propyl] methylamine is known, for example, from U.S. Pat. No. 4,808,605, where its preparation from 4-[1-benzyloxy-N-methylformamido]butyric acid is disclosed.

All other reagents and solvents are readily commercially available, for example from Aldrich Chemical Company or equivalent suppliers.

The Process

The first step is an aldol condensation in which (S)-6-fluoro-1-isopropyl-3,4-dihydro-1H-naphthalen-2-one, compound 1, is converted to (1S,2S)-(6-fluoro-2-hydroxy-1-isopropyl-1,2,3,4-tetrahydronaphthalen-2-yl) acetonitrile, compound 2, by reaction with the anion of acetonitrile. Typically, the acetonitrile anion is prepared by contacting acetonitrile, in solution in an aprotic polar solvent, with approximately one equivalent of a strong base such as an alkyllithium or aryllithium, for example butyllithium, also in solution in an aprotic polar solvent, at a reduced temperature, such as at −78° C. The tetralone (1), also in solution in an aprotic polar solvent, is added gradually to the solution of the acetonitrile anion. The reaction with the acetonitrile anion preferably takes place at reduced temperatures, such as at −78° C.; but may take place at less extreme temperatures, such as at a temperature between about −20° C. and 8° C., if a lithium halide such as lithium chloride (preferred) or lithium bromide, in an excess generally between about two-fold and five-fold based on the acetonitrile anion, is added to the acetonitrile anion solution before the addition of the tetralone (1). A preferred aprotic polar solvent for the formation of the acetonitrile anion and the subsequent reaction with the tetralone (1) is tetrahydrofuran. Following completion of the addition of the tetralone (1), the reaction mixture is allowed to warm, and is then quenched with aqueous acid. The nitrile (2) may be isolated from the reaction mixture by any suitable method: a convenient method is extraction of the nitrile (2) from the quenched reaction mixture into a water-immiscible organic solvent, such as isopropyl acetate, toluene, or the like, followed by evaporation of the solvent. The nitrile (2) may be used in subsequent steps of the process without completion of the isolation, or may be isolated and purified by recrystallization from a non-polar solvent, such as hexane, if desired. The nitrile (2) is new.

In the second step, the nitrile (2) is reductively aminated with [3-(1H-benzimidazol-2-yl)propyl]methylamine, compound 3, in the presence of hydrogen and a hydrogenation catalyst, to form (1S,2S)-2-[2-{[3-(1H-benzimidazol-2-yl) propyl]methylamino}ethyl]-6-fluoro-1-isopropyl-1,2,3,4-tetrahydronaphthalen-2-ol, compound 4. The reaction is carried out under conditions typical for such reactions, i.e., the nitrile (2) and amine (3) are dissolved in a lower alkanol (the nitrite solution may also contain an organic solvent such as the isopropyl acetate or toluene from the first step) in the presence of a weak acid and a hydrogenation catalyst, and the resulting mixture is contacted with hydrogen for a period sufficient to complete the reaction. Suitable hydrogenation catalysts are those active at low pressures, and a preferred hydrogenation catalyst is RANEY® nickel (an activated nickel catalyst prepared from aluminum-nickel alloy); suitable hydrogen pressures are from 2–5 bar, with reaction times depending on the catalyst and its relative concentration. The reaction may be performed portionwise, if desired. A typical isolation procedure for the resulting alcohol (4) involves separation of the solution from the catalyst by decantation or filtration, neutralization of the acid with a weak base, and extraction of the alcohol (4) into a water-immiscible organic solvent. The recovered catalyst may generally be re-used in subsequent reaction cycles with equal efficiency.

The alcohol (4) may be isolated if desired by conventional methods, such as by drying of the solution containing it with a drying agent such as anhydrous sodium sulfate and evaporation of the solvent. However, it will preferably be isolated as an acid addition salt, such as the dioxalate salt. Preparation and isolation of the dioxalate salt may be performed by conventional methods for the formation of acid addition salts. A presently preferred method, using acetic acid as the solvent, is shown in the Example: the use of acetic acid as solvent is valuable in that it gives the dioxalate salt of the alcohol (4) in especially pure form.

In the third step, the alcohol (4) is esterified with methoxyacetic acid or an activated derivative of methoxyacetic acid to form mibefradil, (1S,2S)-2-[2-{[3-(1H-benzimidazol-2-yl) propyl]methylamino}ethyl]-6-fluoro-1-isopropyl-1,2,3,4-tetrahydronaphthalen-2-yl methoxyacetate, compound I, which is typically isolated as an acid addition salt, especially the dihydrochloride salt. This acylation reaction is known from U.S. Pat. No. 4,808,605, where it is performed with methoxyacetyl chloride in chloroform in the presence of ethyl-diisopropylamine; and it will be evident to one of ordinary skill in the art that methoxyacetic acid or other activated derivatives of methoxyacetic acid and other reaction conditions such as are typical in esterification of alcohols may be used. A presently preferred esterification reaction, also using methoxyacetyl chloride, but with toluene as solvent and potassium carbonate sesquihydrate as base, is shown in the Example.

Mibefradil (I) may be isolated as the free base if desired, but will preferably be isolated as an acid addition salt, more preferably as the dihydrochloride salt. The preparation and isolation of mibefradil dihydrochloride may be performed by conventional methods, such as by contacting a solution of mibefradil with a solution of hydrogen chloride in a lower alkanol, followed by crystallization of the salt, as shown in the Example.

The invention is illustrated by the following Example.
Preparation of (1S,2S)-(6-fluoro-2-hydroxy-1 -isopropyl-1,2,3,4-tetrahydronaphthalen-2-yl)-acetonitrile.

A 2.5 molar solution of butyllithium in hexane, 10.8 mL, was added dropwise over 20 minutes through an addition funnel to a solution of 1.4 mL acetonitrile in 10 mL tetrahydrofuran at −78° C. The addition funnel was rinsed with an additional 7 mL tetrahydrofuran; and the solution was stirred at −78° C. for 20 minutes. A solution of 4.99 g (S)-6-fluoro-1-isopropyl-3,4-dihydro-1H-naphthalen-2-one in 10 mL tetrahydrofuran was added dropwise through the addition funnel to the solution at −78° C. over 20 min. The addition funnel was rinsed with an additional 2 mL tetrahydrofuran. The light brown solution was allowed to warm to −10° C. over approximately two hours; and was then quenched with 75 mL 5% aqueous hydrochloric acid. The resulting mixture was transferred to a 500 mL separatory funnel; and the reaction vessel was rinsed with 75 mL isopropyl acetate, which was added to the separatory funnel. The aqueous and organic layers were separated, and the aqueous layer was extracted twice with 75 mL isopropyl acetate. The combined organic layers, containing (1S,2S)-(6-fluoro-2-hydroxy-1-isopropyl-1,2,3,4-tetrahydronaphthalen-2-yl) acetonitrile, were concentrated to approximately 10–15 mL and used as-is in the next step. Toluene may be used in place of isopropyl acetate, if desired.

From a similar preparation in which the nitrile was extracted into diethyl ether instead of isopropyl acetate, the ether solution was dried over anhydrous magnesium sulfate, and the ether removed on a rotary evaporator to give a brown oil, which dried to a beige solid under vacuum drying. A 2.0 g portion of the crude nitrile was recrystallized from hexane to give 1.52 g of pure (1S,2S)-(6-fluoro-2-hydroxy-1-isopropyl-1,2,3,4-tetrahydronaphthalen-2-yl) acetonitrile as a white solid: $^1$H NMR (CDCl$_3$, 300 MHz):δ7.0(1H, m),6.83(2H, m),3.0(1H, dd),2.78(1 H, m),2.69(1H, t),2.6 (1H, s, br, —OH),2.47(2H, ab),2.38(1H, m),2.17(1H, m, ddd),1.97(1H, m),1,14(3H, d), 0.47 (3H, d).

Preparation of (1S,2S)-2-[2-{[3-(1H-benzimidazol-2-yl) propyl]methylamino}ethyl]-6-fluoro-1-isopropyl-1,2,3,4-tetrahydronaphthalen-2-ol.

A solution containing (1S,2S)-(6-fluoro-2-hydroxy-1-isopropyl- 1,2,3,4-tetrahydro-naphthalen-2-yl) acetonitrile was prepared in a graduated cylinder by adding sufficient isopropyl acetate to the (1S,2S)-(6-fluoro-2-hydroxy-1-isopropyl-1,2,3,4-tetrahydro-naphthalen-2-yl) acetonitrile solution from the previous step to bring the total volume to 15 mL, then adding 20 mL methanol.

[3-(1H-Benzimidazol-2-yl)propyl]methylamine, 6.86 g, was dissolved in a mixture of 25 mL methanol and 12 mL isopropyl acetate, and 2.1 mL acetic acid was added to the solution. The solution was added to a Parr hydrogenation bottle; and 28 g of a 50% slurry of RANEY® nickel in water was added, and washed in with 25 mL methanol. Approximately 5 mL of the (1S,2S)-(6-fluoro-2-hydroxy-1-isopropyl-1,2,3,4-tetrahydronaphthalen-2-yl)-acetonitrile solution was added to the mixture in the Parr bottle; and the bottle was shaken for 40 minutes under 3–4 bar hydrogen pressure. The remaining (1S,2S)-(6-fluoro-2-hydroxy-1-isopropyl-1,2,3,4-tetrahydronaphthalen-2-yl) acetonitrile solution was added in 4–5 mL portions (total 8 portions) with 40 minute hydrogenation periods for each addition. After addition of the last portion of the (1S,2S)-(6-fluoro-2-hydroxy-1-isopropyl-1,2,3,4-tetrahydronaphthalen-2-yl) acetonitrile solution to the Parr bottle, the graduated cylinder was rinsed with 5 mL methanol, and the rinsings added to the last hydrogenation step. Following completion of the hydrogenation reaction, the reaction solution containing (1S,2S)-2-[2-{[3-( 1H-benzimidazol-2-yl)propyl]methylamino}ethyl]-6-fluoro-1-isopropyl-1,2,3,4-tetrahydronaphthalen-2-ol was decanted from the Parr bottle and filtered through a thin pad of diatomaceous earth. The residual RANEY® nickel was washed by decantation three times with 40 mL methanol, with 10 min. stirring between decantations; and may then be re-used in subsequent hydrogenation cycles if desired. The combined solution and washings were concentrated under vacuum, and 80 mL water and 16–17 mL saturated aqueous sodium bicarbonate solution were added, raising the pH of the mixture to 7–8. The aqueous mixture was extracted three times with 50 mL toluene; and the combined toluene solution of ( 1S,2S)-2-[2-{[3-(1H-benzimidazol-2-yl)propyl]methylamino }ethyl]-6-fluoro-1-isopropyl- 1,2,3,4-tetrahydronaphthalen-2-ol was concentrated to 15–20 mL and used as-is for the next step.
Preparation of (1S,2S)-2-[2-{[3-( 1H-benzimidazol-2-yl) propyl]methylamino}ethyl]-6-fluoro-1-isopropyl-1,2,3,4-tetrahydronaphthalen-2-ol dioxalate.

Acetic acid, 120 mL, was added to the concentrated toluene solution of (1S,2S)-2-[2-{[3-(1H-benzimidazol-2- yl)propyl]methylamino}ethyl]-6-fluoro-1-isopropyl-1,2,3,4-tetrahydronaphthalen-2-ol from the previous step. An azeotropic mixture of acetic acid and toluene was distilled at ambient pressure until the volume was reduced to about 50 mL. Oxalic acid dihydrate, 5.44 g, was added to the solution, and the solution was stirred at approximately 100° C. for fifteen minutes. The solution was then allowed to cool slowly to 45° C., held at that temperature for two hours, allowed to cool further to 30° C., and held at that temperature for another one hour. A precipitate of (1S,2S)-2-[2-{[3-(1H-benzimidazol-2-yl)propyl]methylamino}3ethyl]-6-fluoro-1-isopropyl-1,2,3,4-tetrahydronaphthalen-2-ol dioxalate formed during this cooling. The mixture was filtered at 30° C., and the warm filtrate was used to rinse residual precipitate onto the filter. The filter cake was washed three times with 10 mL acetic acid at room temperature and dried in a vacuum oven at 55°–60° C. under nitrogen flow for eighteen hours to give 9.32 g (1S,2S)-2-[2-{[3-(1H-benzimidazol-2-yl)propyl]methylamino}ethyl]-6-fluoro-1-isopropyl-1,2,3,4-tetrahydronaphthalen-2-ol dioxalate as a white solid, containing one molecule of acetic acid of crystallization per molecule of the dioxalate acid addition salt, m.p. ~130° C. with decomposition.

Preparation of mibefradil and mibefradil dihydrocloride.

To a 1 L flask was added 41.0 g (actual) (1S,2S)-2-[2-{[3-(1H-benzimidazol-2-yl) propyl]methylamino}ethyl]-6-fluoro-1-isopropyl-1,2,3,4-tetrahydronaphthalen-2-ol dioxalate, 240 mL water, and 240 mL toluene, with stirring. Potassium hydroxide pellets, 22.4 g, were added, and the mixture heated to 45°–50° C. for one hour with continued stirring. The resulting two-phase mixture was separated using a separatory funnel while still warm. The organic phase was washed with 65 mL water and then vacuum filtered through CELATOM® (diatomaceous earth filter agent).

To the organic phase was added 39.4 g (4.0 equivalents) potassium carbonate sesquihydrate; then a solution of 21 0 g (17.7 mL, 3.25 equivalents) methoxyacetyl chloride in 33 mL toluene was added over two hours at 25°–30° C., and the resulting mixture stirred for an additional 30 minutes at that temperature. Water, 200 mL, was added at room temperature to quench the reaction; and the phases separated using a separatory funnel. The organic phase, containing mibefradil as the free base, was washed with 66 mL water. The washed organic phase was vacuum filtered through a pad of CELATOM®; and most of the toluene removed by distillation at 50° C. and 4 mmHg, leaving a solution of mibefradil in approximately 10 mL toluene. Ethanol, 17.8 mL, was added, and the mixture allowed to cool to room temperature.

To the stirred mixture was added a solution of 4.4 g of hydrogen chloride in 44.6 mL (35.0 g) ethanol at 20° C., and then a further 10.2 mL (8.0 g) ethanol. The resulting mixture was heated to 50° C.; and 1.0 mL water was added, followed by a solution of 3.4 mL water in 332 mL methyl tert-butyl ether over one hour. The mixture was stirred for ten minutes at 50° C., seeded with mibefradil dihydrochloride crystals, then stirred at 50° C. for three hours. A solution of 0.6 mL water in 65 mL methyl tert-butyl ether was added over one hour, and the mixture aged for a further 1.5 hours at 50° C. The mixture was then cooled to 15° C. over two hours and aged at 15° C. for a further hour, and the resulting slurry of mibefradil dihydrochloride was filtered on a Buchner funnel and rinsed with 95 mL dry methyl tert-butyl ether. The product was dried in a vacuum oven at 50° C. to yield mibefradil dihydrochloride as the monohydrate in 95% yield.

While this invention has been described in conjunction with specific embodiments and examples, it will be evident to one of ordinary skill in the art, having regard to this disclosure, that equivalents of the specifically disclosed materials and techniques will also be applicable to this invention; and such equivalents are intended to be included within the following claims.

What is claimed is:

1. (6-Fluoro-2-hydroxy-1-isopropyl-1,2,3,4-tetrahydronaphthalen-2-yl)acetonitrile, as an individual isomer or as a racemic or non-racemic mixture of isomers.

2. The compound of claim 1 that is (1S,2S)-(6-fluoro-2-hydroxy-1-isopropyl-1,2,3 ,4-tetrahydronaphthalen-2-yl) acetonitrile.

3. A method of preparing (6-fluoro-2-hydroxy-1-isopropyl-1,2,3,4-tetrahydronaphthalen-2-yl) acetonitrile comprising contacting 6-fluoro-1-isopropyl-3,4-dihydro-1H-naphthalen-2-one with the anion of acetonitrile in an aprotic polar solvent.

4. The method of claim 3 for preparing (1S,2S)-(6-fluoro-2-hydroxy-1-isopropyl-1,2,3,4-tetrahydronaphthalen-2-yl) acetonitrile comprising contacting (S)-6-fluoro-1-isopropyl-3,4-dihydro-1H-naphthalen-2-one with the anion of acetonitrile in an aprotic polar solvent.

5. The method of claim 3 where the aprotic polar solvent comprises tetrahydrofuran.

6. The method of claim 3 where the step of contacting is carried out at approximately −78° C.

7. The method of claim 3 where the step of contacting is carried out at a temperature between about −20° C. and 8° C. in the presence of an excess of a lithium halide.

8. The method of claim 3 where the anion of acetonitrile is prepared by contacting acetonitrile with an alkyllithium or aryllithium.

9. A method of preparing 2-[2-{[3-(1H-benzimidazol-2-yl)propyl]methylamino}ethyl]-6-fluoro-1-isopropyl-1,2,3 ,4-tetrahydronaphthalen-2-ol comprising contacting [3-(1H-benzimidazol-2-yl)propyl]methylamine with (6-fluoro-2-hydroxy-1-isopropyl-1,2,3,4-tetrahydronaphthalen-2-yl) acetonitrile in the presence of hydrogen and a hydrogenation catalyst.

10. The method of claim 9 for preparing (1S,2S)-2-[2-{[3-(1H-benzimidazol-2-yl)-propyl]methylamino}ethyl]-6-fluoro-1-isopropyl-1,2,3,4-tetrahydronaphthalen-2-ol comprising contacting [3-( 1H-benzimidazol-2-yl)propyl] methylamine with (1S,2S)-(6-fluoro-2-hydroxy-1-isopropyl- 1,2,3,4-tetrahydronaphthalen-2-yl) acetonitrile in the presence of hydrogen and a hydrogenation catalyst.

11. The method of claim 9 where the hydrogenation catalyst is RANEY® nickel.

12. The method of claim 9 where the reaction is conducted in the presence of a weak acid.

13. The method of claim 12 where the weak acid is acetic acid.

14. The method of claim 9 further including the step of contacting the thus-formed 2-[2-{[3-(1H-benzimidazol-2-yl)propyl]methylamino}ethyl]-6-fluoro-1-isopropyl-1,2,3,4-tetrahydronaphthalen-2-ol with methoxyacetic acid or an activated derivative of methoxyacetic acid to prepare 2-[2-{[3-(1H-benzimidazol-2-yl)propyl]methylamino}ethyl]-6-fluoro-1-isopropyl- 1,2,3 ,4-tetrahydronaphthalen-2-yl methoxyacetate.

15. The method of claim 10 further including the step of contacting the thus-formed (1S,2S)-2-[2-{[3-(1H-benzimidazol-2-yl)propyl]methylamino}ethyl]-6-fluoro-1-isopropyl-1,2,3,4-tetrahydronaphthalen-2-ol with methoxyacetic acid or an activated derivative of methoxyacetic acid to prepare (1S,2S)-2-[2-{[3-(1H-benzimidazol-2-yl)propyl]methylarnino}-ethyl]-6-fluoro-1-isopropyl-1,2,3,4-tetrahydronaphthalen-2-yl methoxyacetate.

16. The method of claim 14 where the methoxyacetic acid or activated derivative of methoxyacetic acid is methoxyacetyl chloride, and the step of contacting occurs in the presence of a base in an aprotic solvent.

17. The method of claim 14 further including the step of forming an acid addition salt of the 2-[2-{[3-(1H-benzimidazol-2-yl)propyl]methylamino}ethyl]-6-fluoro-1-isopropyl-1,2,3,4-tetrahydronaphthalen-2-yl methoxyacetate.

18. The method of claim 17 where the acid addition salt is the dihydrochloride salt.

19. The method of claim 18 where the step of forming the dihydrochloride salt comprises reacting the 2-[2-{[3-(1H-benzimidazol-2-yl)propyl]methylamino}ethyl]-6-fluoro-1-isopropyl-1,2,3,4-tetrahydronaphthalen-2-yl methoxyacetate with a solution of hydrogen chloride in a lower alkanol.

20. The method of claim 19 where the lower alkanol is ethanol.

* * * * *